United States Patent
Suh et al.

(10) Patent No.: US 7,612,207 B2
(45) Date of Patent: Nov. 3, 2009

(54) METHOD FOR PREPARING CLOPIDOGREL 1,5-NAPHTHALENEDISULFONATE OR HYDRATE THEREOF

(75) Inventors: Kwee Hyun Suh, Suwon-si (KR); Sang Min Yun, Seongnam-si (KR); Eun Sook Kim, Seoul (KR); Gwan Sun Lee, Seoul (KR)

(73) Assignee: Hanmi Pharm. Co., Ltd., Hwaseong-gun (KR)

( * ) Notice: Subject to any disclaimer, the term of this patent is extended or adjusted under 35 U.S.C. 154(b) by 0 days.

(21) Appl. No.: 12/293,959

(22) PCT Filed: Mar. 16, 2007

(86) PCT No.: PCT/KR2007/001307

§ 371 (c)(1), (2), (4) Date: Sep. 22, 2008

(87) PCT Pub. No.: WO2007/108615

PCT Pub. Date: Sep. 27, 2007

(65) Prior Publication Data

US 2009/0036683 A1 Feb. 5, 2009

(30) Foreign Application Priority Data

Mar. 22, 2006 (KR) .................. 10-2006-0026110

(51) Int. Cl.
*C07D 495/04* (2006.01)
(52) U.S. Cl. ...................................... 546/114
(58) Field of Classification Search ............ 546/114
See application file for complete search history.

(56) References Cited

U.S. PATENT DOCUMENTS

2005/0256152 A1    11/2005   Doser et al.

FOREIGN PATENT DOCUMENTS

| KR | 2005099445 A | 10/2005 |
| WO | 2005/080890 A1 | 9/2005 |
| WO | 2005/103059 A1 | 11/2005 |

*Primary Examiner*—Patricia L Morris
(74) *Attorney, Agent, or Firm*—Rothwell, Figg, Ernst & Manbeck, P.C.

(57) ABSTRACT

The present invention relates to a method for preparing clopidogrel 1,5-naphthalenedisulfonate or a hydrate thereof, which comprises reacting a clopidogrel-acid addition salt with disodium 1,5-naphthalenedisulfonate or its hydrate in water, or a mixture of water and an organic solvent. High quality clopidogrel 1,5-naphthalenedisulfonate can be prepared by the inventive method by way of using non-corrosive disodium 1,5-naphthalenedisulfonate.

8 Claims, No Drawings

METHOD FOR PREPARING CLOPIDOGREL 1,5-NAPHTHALENEDISULFONATE OR HYDRATE THEREOF

CROSS REFERENCE TO RELATED APPLICATIONS

This application is a 35 USC § 371 National Phase Entry Application from PCT/KR2007/001307, filed Mar. 16, 2007, and designating the United States. This application claims priority under 35 U.S.C. § 119 based on Korean Patent Application No. 10-2006-0026110 filed Mar. 22, 2006, which is incorporated herein in its entirety.

FIELD OF THE INVENTION

The present invention relates to a method for preparing clopidogrel 1,5-naphthalenedisulfonate or hydrate thereof.

BACKGROUND OF THE INVENTION

Clopidogrel (methyl(S)-(+)-α-(2-chlorophenyl)-6,7-dihydrothieno[3,2-a]pyridine-5(4H)-acetate) of formula (IV), which has inhibiting activity against platelet agglutination, is a useful vascular diseases therapeutic for treating peripheral artery diseases such as stroke, thrombosis and embolism, as well as ischemic heart diseases such as myocardial infarction and angina pectoris:

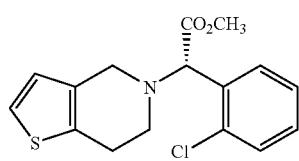

Clopidogrel, an optically active dextrorotatory compound, however, is an oil phase which is unstable under moist and high temperature conditions and is difficult to be purified to the level of required for pharmaceutical use.

Accordingly, acid addition salts of clopidogrel, which are stable solid and easy to purify, have been developed. Clopidogrel 1,5-naphthalenedisulfonate (napadisilate (INN)), one of the most stable acid addition salts, has been disclosed in International Publication No. WO 2005/097804, wherein clopidogrel 1,5-naphthalenedisulfonate is prepared by reacting the free base form of clopidogrel with 1,5-naphthalenedisulfonic acid.

However, 1,5-naphthalenedisulfonic acid used in the above method (Armstrong acid) is a strong acid having a $pK_{a1}$ value of −3.37 and a $pK_{a2}$ of −2.64, and is not suitable for use in the preparation of high quality clopidogrel 1,5-naphthalenedisulfonate due to its corrosiveness, handling in a bulk production process and tendency to color the product red. Accordingly, there has been a need for an improved method of preparing clopidogrel 1,5-naphthalenedisulfonate.

The present inventors have found that clopidogrel 1,5-naphthalenedisulfonate can be beneficially prepared by reacting a clopidogrel acid addition salt with a 1,5-naphthalenedisulfonate, which is not acidic nor corrosive.

SUMMARY OF THE INVENTION

It is an object of the present invention to provide a new method of preparing clopidogrel 1,5-naphthalenedisulfonate, which can ameliorate the problems associated with the conventional methods.

In accordance with an aspect of the present invention, there is provided a method for preparing clopidogrel 1,5-naphthalenedisulfonate of formula (I) or a hydrate thereof, which comprises:

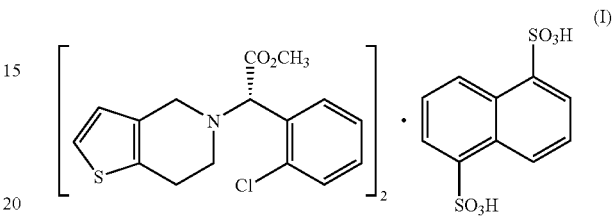

reacting a clopidogrel-acid addition salt of formula (II)

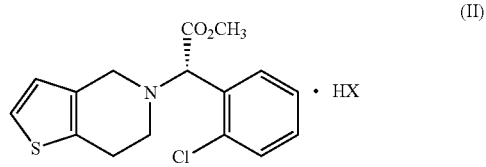

with disodium 1,5-naphthalenedisulfonate of formula (III) or its hydrate

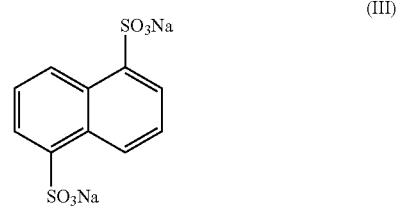

in water, or a mixture of water and an organic solvent, wherein HX is an acid capable of reacting with clopidogrel to form an acid addition salt excluding naphthalenedisulfonate.

DETAILED DESCRIPTION OF THE INVENTION

The method of the present invention is characterized in that disodium 1,5-naphthalenedisulfonate, which is non-corrosive and non-acidic is used as a starting material, instead of 1,5-naphthalenedisulfonic acid.

The inventive method of preparing clopidogrel 1,5-naphthalenedisulfonate of formula (I) or a hydrate thereof may be carried out by adding the clopidogrel-acid addition salt of formula (II) and disodium 1,5-naphthalenedisulfonate of formula (III) to water or a water-organic solvent mixture to obtain a solution or a suspension; stirring the solution or the suspension at a temperature ranging from 0° C. to the boiling point of the solvent used, preferably from room temperature to the boiling point of the solvent used.

Examples of the organic solvent which may be used in the present invention include water-miscible solvents selected from the group consisting of $C_{1-3}$ alcohols such as methanol, ethanol, isopropanol; ketones such as acetone, methyl ethyl ketone, methyl isobutyl ketone; alkyl acetates such as methyl acetate, ethyl acetate, isopropyl acetate; acetonitrile; tetrahydrofuran; and 1,4-dioxane; as well as water-immiscible solvents selected from the group consisting of $C_6$ or higher alkanes such as n-hexane, n-heptane, n-octane, isooctane; dialkyl ethers such as diethyl ether, diisopropyl ether; chloroalkanes such as dichloromethane, 1,2-dichloroethane, chloroform; aromatic solvents such as benzene and toluene; and a mixture thereof. Among those, water-miscible solvents, methanol, ethanol, isopropanol, acetone, methylethylketone, methyl isobutyl ketone, methyl acetate, ethyl acetate, isopropyl acetate, acetonitrile, tetrahydrofuran and 1,4-dioxane are preferred, and methanol, ethanol, isopropanol and acetone are more preferred.

Although the water-organic solvent mixture may have any organic solvent content, the preferred amount of the organic solvent is less than 95% by volume based on the mixture, which helps the removal of the incidental salt.

Disodium 1,5-naphthalenedisulfonate of formula (III) or its hydrate may be employed in an amount ranging from 0.45 to 0.7 mole per mole of clopidogrel acid addition salt of formula (II).

The clopidogrel acid addition salt of formula (II) may be any of those disclosed by European Patent No. 0281459 or International Publication No. WO 2004/074215. Representative examples of the clopidogrel acid addition salt include inorganic acid salts such as hydrochloride, hydrobromide, hydroiodide, hydrogen sulfate, phosphate, perchlorate and nitrate; sulfonates such as methanesulfonate, ethanesulfonate, 1,2-ethanedisulfonate, benzenesulfonate, p-toluenesulfonate, camphorsulfonate, laurylsulfonate, 2-naphthalenesulfonate; alkyl sulfates such as methyl sulfate and ethyl sulfate; organic acid salts such as acetate, oxalate, trifluoroacetate, propionate, benzoate, citrate, tartarate, succinate, malonate, lactate, malate, maleate and fumarate. Preferred among the above are hydrochloride, hydrobromide, hydrogen sulfate, camphorsulfonate and benzenesulfonate of clopidogrel.

The present invention will be described in further detail with reference to Examples. However, it should be understood that the present invention is not restricted by the specific Examples.

Preparation of clopidogrel
1,5-naphthalenedisulfonate monohydrate

EXAMPLE 1

1.0 g of clopidogrel hydrochloride (2.8 mmol) was dissolved in a mixture of 10 ml of methanol and 10 ml of distilled water, and 515 mg of disodium 1,5-naphthalenedisulfonate monohydrate (95%, 1.4 mmol) was added thereto. The resulting solution was stirred at room temperature for 15 hours, and then at 5° C. for 2 hours. The resulting precipitates were filtered under a reduced pressure, washed with 1 ml of a mixture of methanol and distilled water (1/2, v/v), and dried at 50° C. for 4 hours, to obtain 1.1 mg of the title compound (yield: 85%) as a white powder.

M.p.: 221-224° C. (reported value: 223-225° C.);
Water contents (Karl-Fisher titrator): 1.9%; (theoretical value: 1.90%)
Purity (HPLC): 98.7% (purity of standard product: 99.3%)

EXAMPLE 2

3.0 g of clopidogrel hydrochloride (8.4 mmol) and 1.54 g of disodium 1,5-naphthalenedisulfonate monohydrate (95%, 4.2 mmol) were suspended in a mixture of 20 ml of isopropanol and 10 ml of distilled water and the suspension was homogenized at 70° C. The resulting solution was slowly cooled; and stirred at room temperature for 15 hours, and then at 5° C. for 2 hours. The resulting precipitates were filtered under a reduced pressure, washed with 3 ml of a mixture of isopropanol and distilled water (2/1, v/v), and dried at 50° C. for 4 hours, to obtain 3.5 g of the title compound (yield: 88%) as a white powder.

M.p.: 220-224° C. (reported value: 223-225° C.);
Water contents (Karl-Fisher titrator): 1.80%; (theoretical value: 1.90%)

EXAMPLE 3

3.0 g of clopidogrel hydrobromide (7.4 mmol) and 1.37 g of disodium 1,5-naphthalenedisulfonate monohydrate (95%, 3.7 mmol) were suspended in a mixture of 20 ml of isopropanol and 10 ml of distilled water, and the suspension was homogenized at 70° C. The resulting solution was slowly cooled; and stirred at room temperature for 15 hours, and then at 5° C. for 2 hours. The resulting precipitates were filtered under a reduced pressure, washed with 3 ml of a mixture of isopropanol and distilled water (2/1, v/v), and dried at 50° C. for 4 hours, to obtain 3.2 g of the title compound (yield: 91%) as an white powder.

M.p.: 221-224° C. (reported value: 223-225° C.);
Water contents (Karl-Fisher titrator): 2.0%; (theoretical value: 1.90%)

EXAMPLE 4

5.0 g of clopidogrel besylate (10.4 mmol) and 1.92 g of disodium 1,5-naphthalenedisulfonate monohydrate (95%, 5.2 mmol) were suspended in a mixture of 20 ml of methanol and 15 ml of distilled water and the suspension was homogenized at 60° C. The resulting solution was slowly cooled; and stirred at room temperature for 15 hours, and then at 5° C. for 2 hours. The resulting precipitates were filtered under a reduced pressure, washed with 6 ml of a mixture of methanol and distilled water (1/1, v/v), and dried at 50° C. for 4 hours, to obtain 4.6 g of the title compound (yield: 94%) as a white powder.

M.p.: 220-224° C. (reported value: 223-225° C.);
Water contents (Karl-Fisher titrator): 1.75%; (theoretical value: 1.90%)

EXAMPLE 5

5.0 g of clopidogrel besylate (10.4 mmol) and 1.92 g of disodium 1,5-naphthalenedisulfonate monohydrate (95%, 5.2 mmol) were suspended in a mixture of 30 ml of isopropanol and 15 ml of distilled water and the suspension was homogenized at 70° C. The resulting solution was slowly cooled; and stirred at room temperature for 15 hours, and then 5° C. for 2 hours. The resulting precipitates were filtered under a reduced pressure, washed with 6 ml of a mixture of isopropanol and distilled water (2/1, v/v), and dried at 50° C. for 4 hours, to obtain 4.2 g of the title compound (yield: 86%) as a white powder.

M.p.: 220-224° C. (reported value: 223-225° C.);
Water contents (Karl-Fisher titrator): 1.8%; (theoretical value: 1.90%)

EXAMPLE 6

3.0 g of clopidogrel (+)-(1S)-camphor-10-sulfonate (5.4 mmol) and 998 mg of disodium 1,5-naphthalenedisulfonate monohydrate (95%, 2.7 mmol) were suspended in a mixture of 20 ml of isopropanol and 10 ml of distilled water and the suspension was homogenized at 70° C. The resulting solution was slowly cooled; and stirred at room temperature for 15 hours, and then at 5° C. for 2 hours. The resulting precipitates were filtered under a reduced pressure, washed with 3 ml of a mixture of isopropanol and distilled water (2/1, v/v), and dried at 50° C. for 4 hours, to obtain 2.4 g of the title compound (yield: 92%) as a white powder.

M.p.: 220-223° C. (reported value: 223-225° C.);

Water contents (Karl-Fisher titrator): 2.0%; (theoretical value: 1.90%)

EXAMPLE 7

3.0 g of clopidogrel (−)-(1R)-camphor-10-sulfonate (5.4 mmol) and 998 mg of disodium 1,5-naphthalenedisulfonate monohydrate (95%, 2.7 mmol) were suspended in a mixture of 20 ml of isopropanol and 10 ml of distilled water and the suspension was homogenized at 70° C. The resulting solution was slowly cooled; and stirred at room temperature for 15 hours, and then at 5° C. for 2 hours. The resulting precipitates were filtered under a reduced pressure, washed with 3 ml of a mixture of isopropanol and distilled water (2/1, v/v), and dried at 50° C. for 4 hours, to obtain 2.3 g of the title compound (yield: 88%) as an white powder.

M.p.: 221-224° C. (reported value: 223-225° C.);

Water contents (Karl-Fisher titrator): 1.75%; (theoretical value: 1.90%)

EXAMPLE 8

3.0 g of clopidogrel hydrogen sulfate (7.1 mmol) and 1.32 g of disodium 1,5-naphthalenedisulfonate monohydrate (95%, 3.6 mmol) were suspended in a mixture of 20 ml of isopropanol and 10 ml of distilled water and the suspension was homogenized at 70° C. The resulting precipitates were slowly cooled; and stirred at room temperature for 15 hours, and then at 5° C. for 2 hours. The resulting precipitates were filtered under a reduced pressure, washed with 6 ml of a mixture of isopropanol and distilled water (2/1, v/v), and dried at 50° C. for 4 hours, to obtain 3.2 g of the title compound (yield: 94%) as a white powder.

M.p.: 220-223° C. (reported value: 223-225° C.);

Water contents (Karl-Fisher titrator): 1.7%; (theoretical value: 1.90%)

EXAMPLE 9

1.0 g of clopidogrel hydrogen sulfate (2.4 mmol) and 439 mg of disodium 1,5-naphthalenedisulfonate monohydrate (95%, 1.2 mmol) were suspended in a mixture of 5 ml of methanol and 10 ml of distilled water and the suspension was homogenized at 70° C. The resulting solution was slowly cooled; and stirred at room temperature for 15 hours, and then at 5° C. for 2 hours. The resulting precipitates were filtered under a reduced pressure, washed with 6 ml of a mixture of isopropanol and distilled water (2/1, v/v), and dried at 50° C. for 4 hours, to obtain 3.2 g of the title compound (yield: 94%) as a white powder.

M.p.: 220-223° C. (reported value: 223-225° C.);

Water contents (Karl-Fisher titrator): 1.7%; (theoretical value: 1.90%)

EXAMPLE 10

1.0 g of Clopidogrel hydrogen sulfate (2.4 mmol) and 439 mg of disodium 1,5-naphthalenedisulfonate monohydrate (95%, 1.2 mmol) were dissolved in 10 ml of distilled water; and stirred at room temperature for 15 hours, and then at 5° C. for 2 hours. The resulting precipitates were filtered under a reduced pressure, washed with 3 ml of distilled water, and dried at 50° C. for 4 hours, to obtain 0.9 g of the title compound (yield: 84%) as a white powder.

M.p.: 220-223° C. (reported value: 223-225° C.);

Water contents (Karl-Fisher titrator): 2.0%; (theoretical value: 1.90%)

EXAMPLE 11

1.0 g of Clopidogrel hydrogen sulfate (2.4 mmol) and 439 mg of disodium 1,5-naphthalenedisulfonate monohydrate (95%, 1.2 mmol) were suspended in a mixture of 7 ml of toluene and 10 ml of distilled water; and stirred at room temperature for 15 hours, and then at 5° C. for 2 hours. The resulting precipitates were filtered under a reduced pressure, washed with 3 ml of distilled water, and dried at 50° C. for 4 hours, to obtain 0.9 g of the title compound (yield: 84%) as a white powder.

M.p.: 221-224° C. (reported value: 223-225° C.);

Water contents (Karl-Fisher titrator): 1.9%; (theoretical value: 1.90%)

EXAMPLE 12

1.0 g of Clopidogrel hydrogen sulfate (2.4 mmol) and 439 mg of disodium 1,5-naphthalenedisulfonate monohydrate (95%, 1.2 mmol) were suspended in a mixture of 7 ml of diethyl ether and 10 ml of distilled water; and stirred at room temperature for 15 hours, and then at 5° C. for 2 hours. The resulting precipitates were filtered under a reduced pressure, washed with 3 ml of distilled water, and dried at 50° C. for 4 hours, to obtain 0.91 g of the title compound (yield: 85%) as a white powder.

M.p.: 221-224° C. (reported value: 223-225° C.);

Water contents (Karl-Fisher titrator): 1.8%; (theoretical value: 1.90%)

As discussed above, the present invention provides an easy method for preparing clopidogrel 1,5-naphthalenedisulfonate or its hydrate on a large scale, in which disodium 1,5-naphthalenedisulfonate, a non-corrosive and non-coloring starting material is used without any of the problems encountered in the conventional method.

While the invention has been described with respect to the above specific embodiments, it should be recognized that various modifications and changes may be made to the invention by those skilled in the art which also fall within the scope of the invention as defined by the appended claims.

What is claimed is:

1. A method for preparing clopidogrel 1,5-naphthalenedisulfonate of formula (I) or a hydrate thereof, which comprises:

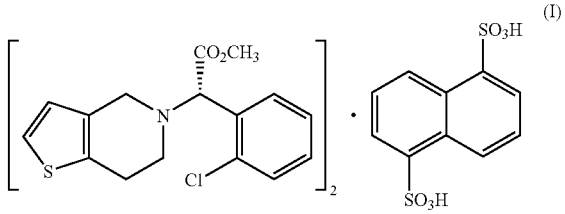

reacting a clopidogrel-acid addition salt of formula (II)

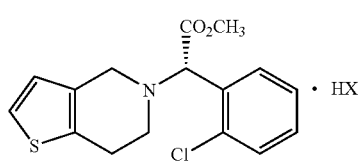

with disodium 1,5-naphthalenedisulfonate of formula (III) or its hydrate

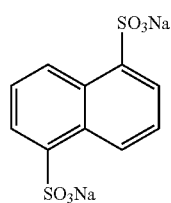

in water, or a mixture of water and an organic solvent, wherein HX is an acid capable of reacting with clopidogrel to form an acid addition salt excluding naphthalenedisulfonate.

2. The method of claim 1, wherein the organic solvent is selected from the group consisting of $C_{1-3}$ alkyl alcohols, ketones, alkyl acetates, acetonitrile, tetrahydrofuran, 1,4-dioxane, $C_6$ or higher alkanes, dialkyl ethers, chloroalkanes and aromatic solvents.

3. The method of claim 2, wherein the organic solvent is selected from the group consisting of methanol, ethanol, isopropanol, acetone, methyl ethyl ketone, methyl isobutyl ketone, methyl acetate, ethyl acetate, isopropyl acetate, acetonitrile, tetrahydrofuran and 1,4-dioxane.

4. The method of claim 3, wherein the organic solvent is selected from the group consisting of methanol, ethanol, isopropanol and acetone.

5. The method of claim 1, wherein the mixture of water and the organic solvent comprises the organic solvent in amount of less than 95% by volume based on the mixture.

6. The method of claim 1, wherein disodium 1,5-naphthalenedisulfonate of formula (III) or its hydrate is employed in an amount ranging from 0.45 to 0.7 equivalent based on the acid addition salt of formula (II).

7. The method of claim 1, wherein HX is an acid which forms an acid addition salt selected from the group consisting of inorganic acid salts, sulfonates, alkyl sulfates and organic acid salts.

8. The method of claim 7, wherein the acid addition salt is selected from the group consisting of hydrochloride, hydrobromide, hydrogen sulfate, benzene sulfonate and camphorsulfonate.

* * * * *